United States Patent
Xu et al.

(10) Patent No.: US 12,036,364 B2
(45) Date of Patent: Jul. 16, 2024

(54) MOISTURE DISSIPATING CARTRIDGE AND BREATHING CIRCUIT AND BREATHING SYSTEM CONTAINING SUCH A CARTRIDGE

(71) Applicant: VINCENT MEDICAL (DONG GUAN) MANUFACTURING CO., LTD, Guangdong (CN)

(72) Inventors: Jiebing Xu, Guangdong (CN); Zhenxiang Hu, Guangdong (CN); Haibin Yu, Guangdong (CN); Ki Cheung To, Guangdong (CN)

(73) Assignee: VINCENT MEDICAL (DONG GUAN) MANUFACTURING CO., LTD, Guangdong (CN)

( * ) Notice: Subject to any disclaimer, the term of this patent is extended or adjusted under 35 U.S.C. 154(b) by 961 days.

(21) Appl. No.: 17/043,152

(22) PCT Filed: Apr. 3, 2019

(86) PCT No.: PCT/CN2019/081256
§ 371 (c)(1),
(2) Date: Sep. 29, 2020

(87) PCT Pub. No.: WO2019/192521
PCT Pub. Date: Oct. 10, 2019

(65) Prior Publication Data
US 2021/0146077 A1     May 20, 2021

(30) Foreign Application Priority Data
Apr. 3, 2018  (CN) .......................... 201820473795.1

(51) Int. Cl.
*A61M 16/00* (2006.01)
*A61K 31/137* (2006.01)
(Continued)

(52) U.S. Cl.
CPC ....... *A61M 16/0093* (2014.02); *A61K 31/137* (2013.01); *A61K 33/44* (2013.01);
(Continued)

(58) Field of Classification Search
CPC ............ A61M 16/0093; A61M 16/142; A61M 16/0816; A61M 16/0875; A61M 16/161;
(Continued)

(56) References Cited

U.S. PATENT DOCUMENTS 2,269,461 A * 1/1942 Lehmberg ............... A62B 23/02
55/501
3,778,971 A * 12/1973 Granger ............. B01D 19/0031
604/126

(Continued)

FOREIGN PATENT DOCUMENTS

| CN | 104649447 A | 5/2015 |
| CN | 204379943 U | 6/2015 |

(Continued)

OTHER PUBLICATIONS

Translation of written description and claims of CN207836822U via espacenet (Year: 2018).*

(Continued)

*Primary Examiner* — Michael R Reid
*Assistant Examiner* — Tyler A Raubenstraw
(74) *Attorney, Agent, or Firm* — Renner, Kenner, Greive, Bobak, Taylor & Weber (57) ABSTRACT

A breathing circuit having a semipermeable membrane, an outer cage, and optionally an inner cage. The semipermeable membrane contains a poly(tetrafluoroethylene) membrane and a graphene anti-bacterial compound. The semipermeable membrane is affixed to the outer cage; optionally between the inner cage and the outer cage. Breathing circuits and breathing systems may contain such a cartridge.

17 Claims, 4 Drawing Sheets

(51) Int. Cl.
*A61K 33/44* (2006.01)
*A61M 16/08* (2006.01)
*A61M 16/14* (2006.01)
*A61M 16/16* (2006.01)

(52) U.S. Cl.
CPC .... *A61M 16/0816* (2013.01); *A61M 16/0875* (2013.01); *A61M 16/142* (2014.02); *A61M 16/161* (2014.02); *A61M 2205/0205* (2013.01); *A61M 2205/18* (2013.01); *A61M 2205/3334* (2013.01); *A61M 2205/3368* (2013.01); *A61M 2205/7527* (2013.01); *A61M 2240/00* (2013.01)

(58) Field of Classification Search
CPC ...... A61M 2205/0205; A61M 2205/18; A61M 2205/3334; A61M 2205/3368; A61M 2205/7527; A61M 2240/00; A61M 16/105; A61M 16/106; A61M 16/107; A61M 16/1055; A61M 2205/75; A61K 31/137; A61K 33/44

See application file for complete search history.

(56) References Cited

U.S. PATENT DOCUMENTS

| | | | | |
|---|---|---|---|---|
| 5,367,604 A * | 11/1994 | Murray | ............... | A61M 16/109 392/394 |
| 6,044,843 A * | 4/2000 | O'Neil | ................ | A61M 16/08 128/207.14 |
| 7,621,983 B2 * | 11/2009 | Neri | ................ | B01D 19/0031 96/9 |
| 8,561,609 B2 * | 10/2013 | Donovan | ............ | A61M 15/001 128/203.15 |
| 9,415,180 B2 * | 8/2016 | Persson | ............... | A61M 16/047 |
| 10,124,299 B2 * | 11/2018 | Kim | ................ | B01D 71/0211 |
| 10,287,184 B2 * | 5/2019 | Awad | .................... | C02F 1/004 |
| 2005/0263150 A1 * | 12/2005 | Chathampally | ....... | A61M 16/06 128/200.14 |
| 2006/0012057 A1 * | 1/2006 | Anthony | ............. | A61M 16/142 261/154 |
| 2009/0000620 A1 * | 1/2009 | Virr | ....................... | A61M 16/16 261/150 |
| 2009/0056715 A1 * | 3/2009 | Cortez, Jr. | .......... | A61M 16/162 128/203.26 |
| 2012/0136269 A1 * | 5/2012 | Weckstrom | ............ | A61B 5/097 73/23.3 |
| 2012/0271187 A1 * | 10/2012 | McNeill | ................. | A61B 5/097 600/532 |
| 2012/0285448 A1 * | 11/2012 | Dugan | .............. | A61M 16/0605 128/202.16 |
| 2012/0285457 A1 * | 11/2012 | Mansour | ........... | A61M 16/0694 128/205.12 |
| 2015/0101600 A1 * | 4/2015 | Miller | ................. | A61M 16/161 128/203.14 |
| 2016/0045685 A1 * | 2/2016 | Hyde | ................... | A61M 15/008 128/200.14 |
| 2016/0106935 A1 * | 4/2016 | Sezan | ............... | A61M 15/0066 128/203.14 |
| 2016/0114121 A1 * | 4/2016 | Holley | .............. | A61M 16/0066 128/205.12 |
| 2016/0136379 A1 * | 5/2016 | Foley | ................ | A61M 15/0068 128/200.23 |
| 2017/0049987 A1 * | 2/2017 | Higginbotham | .. | A61M 16/0875 |
| 2017/0050996 A1 * | 2/2017 | Cui | ...................... | A61C 8/0013 |
| 2017/0266399 A1 * | 9/2017 | Campana | ............ | A61M 16/107 |
| 2018/0078728 A1 * | 3/2018 | Holyoake | ........... | A61M 16/109 |
| 2018/0085548 A1 * | 3/2018 | Cox | ....................... | A61M 16/22 |
| 2018/0319943 A1 * | 11/2018 | Liu | ....................... | C09D 169/00 |
| 2019/0099576 A1 * | 4/2019 | Lee | ........................ | A61B 5/097 |
| 2019/0209792 A1 * | 7/2019 | Nicoll | ............... | A61M 15/0018 |
| 2019/0290496 A1 * | 9/2019 | Brownhill | ............. | A61M 1/966 |
| 2019/0336714 A1 * | 11/2019 | Vazales | .................. | A61B 1/122 |

FOREIGN PATENT DOCUMENTS

| | | | | |
|---|---|---|---|---|
| CN | 206652059 U | | 9/2016 | |
| CN | 106345180 A | * | 1/2017 | ............. B01D 39/08 |
| CN | 206652059 U | | 11/2017 | |
| CN | 207836822 U | * | 9/2018 | |
| EP | 1867357 A1 | * | 12/2007 | .......... A61M 11/041 |
| EP | 2567938 A1 | | 3/2013 | |
| EP | 3398620 A1 | * | 11/2018 | ............. A61L 27/08 |
| GB | 2297914 A | * | 8/1996 | .......... A61M 16/109 |
| WO | WO-2005058403 A1 | * | 6/2005 | .......... A61M 16/047 |
| WO | WO-2006055860 A2 | * | 5/2006 | .......... A61M 16/0447 |
| WO | WO-2015066562 A2 | * | 5/2015 | .......... A61B 5/0024 |
| WO | 2017044845 A1 | | 3/2017 | |
| WO | 2018046002 A1 | | 3/2018 | |

OTHER PUBLICATIONS

Translation of written description and claims of CN106345180A via espacenet (Year: 2016).*

Search Report of the European Patent Office dated Nov. 30, 2021, 7 pages.

English translation of Japanese Patent Office Action dated Jan. 5, 2022, 4 pages.

* cited by examiner

MOISTURE DISSIPATING CARTRIDGE AND BREATHING CIRCUIT AND BREATHING SYSTEM CONTAINING SUCH A CARTRIDGE

FIELD OF THE INVENTION

The present invention relates to a breathing circuit. More specifically, the present invention relates to an improvement to a breathing circuit which reduces moisture condensation.

BACKGROUND

Assisted breathing circuits such as seen in WO 2011/077250 A1 to Fisher & Paykel published on 30 Jun. 2011, and components therefor such as seen in CN 10621593 A to Vincent Medical published on 14 Dec. 2016, are known for providing users; or patients, with air, typically pumped air, to help them breathe. Breathing circuits often are attached to a breathing system having, for example, a machine (e.g., a ventilator, a pump, a humidifier, a heater, a continuous positive airway pressure (a.k.a., CPAP) machine, etc. and a combination thereof) and lead from the breathing system machine to the user and then may further lead back to the breathing system machine or elsewhere. Oftentimes, the breathing system machine may also heat and/or humidify the air so as to make it easier and/or more comfortable for the user to breathe.

A common problem with breathing circuits is therefore the heat loss between the machine and the user. Heat loss as air moves from the machine to the user is undesirable because it increases the total energy requirements for a machine. Thus, it is desirable to minimize heat loss in a breathing circuit from the machine to the user.

However, to minimize heat loss, the breathing circuits typically are made with relatively thick side walls. This in turn increases the weight of the breathing circuit as a whole. As breathing circuits are typically provided to users who are frail to begin with, any additional weight added to the breathing circuit is to be avoided if possible as it may unduly increase physical strain on the user. Such a weight concern is especially important with, for example, neonatal breathing circuits.

In addition, condensation formation in the tube either before or after the air reaches the user is a problem as well. Condensation upstream of the user reduces the humidity in the air actually breathed in by the user. This in turn requires more energy to generate a higher humidity upstream of the user and therefore may waste both energy and water. Condensation either upstream or downstream of the user may cause a problem as it may increase the weight of the tube as it is absorbed therein, and/or pool in the tube. As noted above, such additional weight is undesirable.

In addition, liquid water in a breathing circuit could lead to the growth of undesirable mould, bacteria, etc. Due to the potential for mould, bacteria, etc. to infect the user and/or otherwise cause complications in those who are frail or have compromised immune systems to begin with, it is typically desirable to minimize such contaminants in a breathing circuit. This is a concern even if the water is absorbed into the surface of the breathing circuit itself, as mould or bacteria could then grow on the surface of the breathing circuit, such as on/in the tube.

It has also been found that when typical breathing circuits absorb water, the plastic surfaces may become wrinkled presumably due to swelling of the plastic by moisture. This wrinkling may turn may affect the breathing circuit's physical properties, such as, for example, moisture release, physical fit to the rest of the breathing circuit, etc.

Furthermore, condensed water pooling in the tube upstream of the user is especially a problem, as this water could then cause a blockage in the user's breathing circuit and/or even flow into the user's windpipes/throat which is undesirable.

Accordingly, there remains the need for an improved breathing circuit which releases moisture from the air inside of the breathing circuit. There also exists the need for an improved breathing circuit which does not absorb as much moisture from the air inside of the breathing circuit. There also exists the need for an improved breathing circuit which has reduced wrinkling during use. There also exists the need for a breathing circuit having a lower chance of contamination. There also exists the need for a cartridge; or a disposable cartridge, which can enhance and/or provide one or more of these benefits.

SUMMARY OF THE INVENTION

An embodiment of the present invention relates to a cartridge for a breathing circuit having a semipermeable membrane, an outer cage, and optionally an inner cage. The semipermeable membrane contains a poly(tetrafluoroethylene) membrane and a graphene anti-bacterial compound. The semipermeable membrane is affixed to the outer cage; optionally between the inner cage and the outer cage.

An embodiment of the present invention also relates to a breathing circuit containing the cartridge herein. An embodiment of the present invention also relates to a breathing system containing the breathing circuit herein.

Without intending to be limited by theory, it is believed that the present invention may, for example, allow moisture, especially moisture downstream from a patient, to dissipate to the atmosphere from the interior of a breathing circuit, so as to reduce condensation within the breathing circuit. This in turn may reduce the weight of the breathing circuit, reduce bacterial contamination of the breathing circuit, and/or reduce wrinkling of the breathing circuit during use, and especially during prolonged and/or repetitive use.

DESCRIPTION OF THE PREFERRED EMBODIMENTS

Unless otherwise specifically provided, all tests herein are conducted at standard conditions which include a room and testing temperature of 25° C., sea level (1 atm.) pressure, and all measurements are made in metric units. Furthermore, all percentages, ratios, etc. herein are by weight, unless specifically indicated otherwise.

In an embodiment of the present invention a cartridge for a breathing circuit contains a semipermeable membrane, an outer cage, and optionally an inner cage interior to the outer cage. The semipermeable membrane contains a poly(tetrafluoroethylene) membrane and a graphene anti-bacterial coating and is affixed to the outer cage, or optionally between the inner cage and the outer cage.

The semipermeable membrane allows water vapour to exit from the cartridge into the environment, while maintaining the overall air pressure within the cartridge. Poly (tetrafluoroethylene) membranes are well-known in the art and available from many suppliers, worldwide, such as Sigma-Aldrich, in a variety of grades, thicknesses, pore sizes, etc. In an embodiment herein, the poly(tetrafluoroethylene) membrane has a thickness of from about 1 μm to about 1 mm; or from about 5 μm to about 750 μm; or from about 10 μm to about 500 μm; or from about 25 μm to about 250 μm. In an embodiment herein, the poly(tetrafluoroethylene) membrane has a water vapour transmission rate (WVTR) of from about 10 g $H_2O$/(hour×$m^2$) to about 1000 g $H_2O$/(hour×$m^2$); or from about 50 g $H_2O$/(hour×$m^2$) to about 800 g $H_2O$/(hour×$m^2$); or from about 100 g $H_2O$/ (hour×$m^2$) to about 650 g $H_2O$/(hour×$m^2$) when measured according to the ASTM F1249-13 test. In an embodiment, the poly(tetrafluoroethylene) membrane has a WVTR of at least 325 g $H_2O$/(hour×$m^2$). In the above, "$m^2$" refers to the surface area of the poly(tetrafluoroethylene) membrane. As one skilled in the art understands, the overall WVTR of a material may be dependent upon many factors, such as the temperature, pore size, material thickness, surface area, humidity, air pressure, air flow rate on both sides of the membrane, etc. In contrast, the WVTR of the cartridge may dependent upon all of these factors as well as the percentage of the semipermeable membrane that is not physically covered (i.e., occluded) by the inner cage and/or the outer cage. One skilled in the art understands that in many cases if the semipermeable membrane is covered by significant portions of either the inner cage and/or the outer cage, and specifically the boundaries (see FIG. 1 at 22) of the inner cage and/or the outer cage, then the boundaries would physically block that portion of the semipermeable membrane, and therefore water vapour would be partially or even completely hindered in passing through that portion, thereby possibly rendering it (at that point) essentially impermeable to water vapour at that point.

In an embodiment herein, the semipermeable membrane; or the poly(tetrafluoroethylene) membrane, has a surface area; or a 2D surface area, of from about 5 $cm^2$ to about 100 $cm^2$; or from about 8 $cm^2$ to about 75 $cm^2$; or from about 10 $cm^2$ to about 60 $cm^2$. In an embodiment herein, the semipermeable membrane; or the poly(tetrafluoroethylene) membrane, measures from about 1 cm to about 25 cm; or from about 1.5 cm to about 20 cm; or from about 2 cm to about 15 cm in width and from about 1 cm to about 10 cm; or from about or from about 1.5 cm to about 7.5 cm; or from about 2 cm to about 5 cm in height. As used herein, "width" indicates a dimension of the semipermeable membrane as measured in the circumferential direction when the semipermeable is installed in a breathing circuit—i.e., in a direction that is radial to the direction of the gas flow. As used herein, "height" indicates a dimension of the semipermeable membrane as measured in the direction of the gas flow, when the semipermeable is installed in a breathing circuit.

In an embodiment herein, the poly(tetrafluoroethylene) membrane alone has a thickness of from about 0.05 mm to about 0.4 mm; or from about 0.07 mm to about 0.2 mm; or from about 0.08 mm to about 0.12 mm; or about 0.1 mm. The density of the poly(tetrafluoroethylene) membrane may be from about 80 g/$m^2$ to about 120 g/$m^2$; or from about 85 g/$m^2$ to about 115 g/$m^2$; or from about 90 g/$m^2$ to about 110 g/$m^2$; or from about 95 g/$m^2$ to about 105 g/$m^2$; or about 100 g/$m^2$.

In an embodiment herein, the impermeability of poly (tetrafluoroethylene) membrane to gas in one minute is from about 3 kPa to about 10 kPa; or from about 4.5 kPa to about 8.5 kPa; or from about 5.5 kPa to about 7 kPa; or about 6 kPa.

Without intending to be limited by theory, it is believed that poly(tetrafluoroethylene) membrane is exceptionally suitable for the present invention for the following reasons: it possesses good thermal stability, particularly being resistant against temperature change in a temperature range of −20° C. to 55° C., and therefore it is useful for long-term transportation or storage. Also, it has excellent acid and alkali resistance and tensile strength. When a drug is added to the breathing circuit, e.g. the drug is carried by the respiratory gas, the respiratory gas may become slightly acidic or alkaline depending on the drug added. The acid and alkali resistance of the membrane minimizes the risk of acid and alkali erosion of the membrane, and thereby prolonging the shelf-life of the membrane. Further, it is believed that poly(tetrafluoroethylene) membrane has good tensile strength and thus is resistant to deformation.

In an embodiment herein, the poly(tetrafluoroethylene) membrane has a tensile strength of at least 0.1 MPa, at least 0.15 MPa; or at least 0.2 MPa in machine direction, and a tensile strength of at least 0.1 MPa; or at least 0.15 MPa; or at least 0.2 MPa in the transverse direction. The tensile strength is measured in accordance with the Standard GB/T 10654-2001. The elongation at break of the poly(tetrafluoroethylene) membrane is at least 5%; or at least 8%; or at least 10%; or at least 11% in machine direction, and at least 20%; or at least 30%; or at least 40% in the transverse direction. The elongation at break is measured in accordance with the Standard GB/T 10654-2001. The high value of tensile strength and elongation at break allow a poly(tetrafluoroethylene) membrane to work well with the graphene anti-bacterial compound particularly the one coated thereon.

Further, the poly(tetrafluoroethylene) membrane has a thermal expansion rate of less than or equal to 30%; or less than or equal to 20%; or less than or equal to 15% in the machine direction, and in the transverse direction, when the membrane is subject to heating at 110° C. for 1 hour.

The semipermeable membrane also contains a graphene anti-bacterial compound which may be, for example, integrated into the poly(tetrafluoroethylene) membrane at the time of membrane formation, and/or may be added to the poly(tetrafluoroethylene) membrane after formation. If the graphene anti-bacterial compound is integrated into the poly(tetrafluoroethylene) membrane at the time of membrane formation, then the graphene anti-bacterial compound may be, for example, pre-mixed with the poly(tetrafluoroethylene) before or during the membrane is formed.

If the graphene anti-bacterial compound is added to the poly(tetrafluoroethylene) membrane after formation, then this is typically via a spraying process, a dipping process, and a combination thereof; or a spraying process.

In an embodiment herein, the graphene anti-bacterial compound is added to a semipermeable membrane containing poly(tetrafluoroethylene) by spraying after the semipermeable membrane is formed.

In an embodiment herein, the graphene anti-bacterial compound may be provided in a mixture to be applied to the semipermeable membrane. The mixture contains from about 0.1% to about 1% of a graphene anti-bacterial compound, from about 90% to about 99% of a thermoplastic elastomer, and from about 0.1% to about 0.5% of an additional anti-bacterial compound; and optionally from about 0.5% to about 5% of an antioxidant, and optionally from about 0.5% to about 5% of an additive, based on the total weight of the mixture. The graphene anti-bacterial compound may be graphene; or a graphene nano-platelet. The thermoplastic elastomer may be styrenic block copolymer thermoplastic elastomer, thermoplastic polyurethane, thermoplastic polyurethane or the like. Also, in an embodiment herein, the mixture may include one or more additives selected from the group consisting of a diluent, a solvent, a catalyst, a dispersant, a defoamer, a thickener, a plasticizer, a stabilizer, a crosslinking agent, an anti-static agent and the like.

The additional anti-bacterial compound may be benzylamine hydrochloride or a quaternary ammonium compound selected from, for example, benzalkonium chloride, benzethonium chloride, cetalkonium chloride, cetylpyridinium chloride, cetrimonium, cetrimide, dofanium chloride, didecyldimethylammonium chloride and domiphen bromide, methylbenzethonium chloride, tetraethylammonium bromide, and a combination thereof.

In an embodiment herein, the mixture contains from about 0.1% to about 0.5% of graphene nano-platelets, from about 90% to about 98% of styrenic block copolymer thermoplastic elastomer, from about 0.1% to about 0.3% of benzylamine hydrochloride, from about 0.5% to about 2% of an antioxidant, and from about 1% to about 5% of an additive, based on the total weight of the mixture. When the mixture is applied to the semipermeable membrane by, for example, spraying, the mixture solidifies and forms a layer, typically a coating on the semipermeable membrane. In an embodiment herein, the formed layer containing the graphene anti-bacterial compound has a thickness of from about 0.01 µm to about 25 µm; or from about 0.1 µm to about 20 µm, or from about 0.5 µm to about 15 µm; or from about 1 µm to about 10 µm.

The molecules in the mixture may interact and form bonds, for example the hydrophilic molecules may form hydrogen bonds, ionic bonds and/or covalent bonds with the graphene compound or other molecules present in the mixture via, for example, by containing polar functional groups. The hydrophilic and hydrophobic groups of the molecules in the layer may contribute to the formation of water-permeable channels in the layer. The polar functional groups useful herein include, but are not limited to, a hydroxyl group, a carboxyl group, an alkoxy group, an aryloxy group, an amino group, a phosphate group such as —$PO_3H_2$, a sulfur-containing group such as —SH, and a combination thereof. The water-permeable channels, which may be present as hydrophilic pores, may allow water molecules to pass through particularly from a higher vapour pressure region to a lower vapour pressure region. Accordingly, the layer is selectively permeable. If present, then the hydrophilic pores have an average diameter of from about 1 nm; or less than about 1 nm; or less than 1 nm.

Without intending to be limited by theory it is believed that the graphene anti-bacterial compound reduces the chance that bacteria will grow on or in the semipermeable membrane. Also, in an embodiment where a layer containing the graphene anti-bacterial compound is formed on the semipermeable membrane, the presence of the small hydrophilic pores in the layer substantially prevent or minimize the chances that bacteria and/or viruses pass the semipermeable membrane. Particularly, it is believed that the hydrophilic pores having an average diameter of less than about 1 nm are effective in blocking the entry of bacteria or viruses having an average diameter of above 1 nm into the cartridge, and preventing bacteria or viruses with said diameter in the respiratory gas from leaving the cartridge. In general, bacteria have a diameter of from about 0.5 μm to 10 μm and viruses have a diameter of from about 20 nm to 450 nm. Accordingly, it is believed that the semipermeable membrane of the present invention can effectively reduce contamination caused by external bacteria or viruses and minimize the risk of spreading these pathogens to the surrounding environments. This in turn reduces the chances of bacterial growth in the cartridge from transmitting to, and then contaminating the user or other surfaces.

Further, in an embodiment where the layer contains additional anti-bacterial compound such as benzylamine hydrochloride or a quaternary ammonium compound as described above, the layer can further inhibit or kill bacteria and/or viruses which are being in contact with the layer. This further enhances the resistance against mold and improves the anti-microbial activity of the semipermeable membrane.

The inner cage, the outer cage, the breathing circuit, etc. may be formed of a metal, a plastic and a combination thereof; or plastic, a resin and a combination thereof; or polyethylene, polypropylene, polystyrene, and a combination thereof; or polyethylene, polypropylene, and a combination thereof. In an embodiment herein, the cartridge contains polystyrene. In an embodiment herein, a plastics are preferred from a cost, hygiene, and formability standpoint, especially from a hygiene standpoint, as they are easily sanitized via known one or more sanitizing processes known in the art such as by employing heat, chemicals, radiation, etc. Furthermore, the inner cage, outer cage, breathing circuit, etc. may be formed by one or more processes known in the art, such as blow moulding, thermo forming, extrusion, etc. in an embodiment of the present invention, the inner and outer cages are formed of polyethylene, as it is believed that these are easier to recycle when combined with the poly(tetrafluoroethylene) membrane.

The inner cage and/or the outer cage may be formed as a fine mesh; with or without thicker, distinct boundaries defining discrete cells, etc. as desired. However, it is recognized that the inner cage and/or the outer cage must have at least some; or a majority, of the open spaces that match up so as to allow water vapour to pass through, in sequence, the inner cage (if present), the semipermeable membrane, and the outer cage so as to be released into the environment.

In an embodiment herein, the semipermeable membrane is formed of a poly(tetrafluoroethylene) membrane that is permeable to both water vapour and respiratory gases. At least one layer of the semipermeable membrane, which is permeable to water vapour but not water, contains a layer of the graphene anti-bacterial compound. Preferably, the layer of the graphene anti-bacterial compound as described above is applied via a spraying process, a dipping process, or a combination thereof, to the poly(tetrafluoroethylene) membrane. The poly(tetrafluoroethylene) membrane in this embodiment further acts as a supporting structure for holding the anti-bacterial graphene compound. The selective permeability of the layer containing graphene anti-bacterial compound renders the resultant semipermeable membrane to be impermeable or less permeable to gases, i.e. mainly allows water vapour to pass through. Also, the poly(tetrafluoroethylene) membrane has good physical properties which allow it to be resistant to deformation. In particular, the poly(tetrafluoroethylene) membrane is porous allowing sufficiently small molecules to pass through. When a layer containing the graphene anti-bacterial compound is applied on the poly(tetrafluoroethylene) membrane, said layer covers the pores on the poly(tetrafluoroethylene) membrane. It is believed that during use, the increase of vapour pressure inside the cartridge may expand the poly(tetrafluoroethylene) membrane, which may at the same time expand the pores in the poly(tetrafluoroethylene) membrane. Provided that the poly(tetrafluoroethylene) membrane has good tensile strength, although the pores may expand, their degree of expansion is within an acceptable range and will not break the layer coated on the poly(tetrafluoroethylene) membrane. The inventors performed tests by replacing poly(tetrafluoroethylene) membrane with other materials, and found that other materials, such as the perfluorinated sulfonic-acid (PFSA) membrane used in CN106215293A, do not work well with the graphene anti-bacterial compound e.g. the water vapour transmission rate is lower with PFSA membrane. Some of the other materials even break the coating layer of the graphene anti-bacterial compound due to expansion.

It has unexpectedly been found that the semipermeable membrane of the present invention possesses good water permeability which helps to remove water vapour from the cartridge and from the semipermeable membrane itself. The membrane is capable of removing excessive water vapour and thus will not crumple. Contrary to the semipermeable membrane of the present invention, a PFSA membrane has a lower water vapour transmission rate and can easily crumple after frequent use.

In an alternative embodiment herein, the semipermeable membrane is formed of a poly(tetrafluoroethylene) membrane that is permeable to only water vapour, while the graphene anti-bacterial compound is permeable to both water vapour and respiratory gases.

In an embodiment herein, the semipermeable membrane is affixed; or removably-affixed, to the outer cage such that the semipermeable membrane covers the open cells. The semipermeable membrane may, for example, be a sheet that covers both the open cells as well as the boundaries or may be affixed so as to only cover the open cells. This may be done by, for example, affixing the semipermeable membrane to the boundaries, and/or the edges of the open cells.

In an embodiment herein, an inner cage is present and the semipermeable membrane is affixed between the inner cage and the outer cage. The semipermeable membrane may be permanently affixed between the inner cage and the outer cage, or may be removably-affixed between the inner cage and the outer cage, as desired. If the semipermeable membrane is permanently-affixed between the inner cage and the outer cage, then this may be done in a variety of ways, such as, for example, permanently affixing the semipermeable membrane to either the inner cage, and/or the outer cage, and then sealing the outer cage in a location exterior of the inner cage, permanently sealing the outer cage in a location exterior to the inner cage, etc. One advantage of having the semipermeable membrane being removably-affixed is that in the case where the semipermeable membrane is worn, torn, punctured, contaminated, or otherwise rendered inoperable, it may be possible to replace; or easily-replace, only the semipermeable membrane, rather than having to replace the entire cartridge. A removably-affixed semipermeable membrane may also provide a benefit when, for example, the cartridge is to be recycled.

The inner cage and/or the outer cage may be affixed to, for example, an upstream connector and/or a downstream connector. It is recognized that depending on the actual construction of the cartridge, the upstream connector and/or the downstream connector may be directly or indirectly connected to the outer cage, and/or the inner cage, as desired. The upstream connector and/or the downstream connector may also be attachable; or removably-attachable; or attached, to a breathing circuit. Typically, both the upstream connector and the downstream connector are attachable; or removably-attachable, to a breathing circuit.

Figure 1:
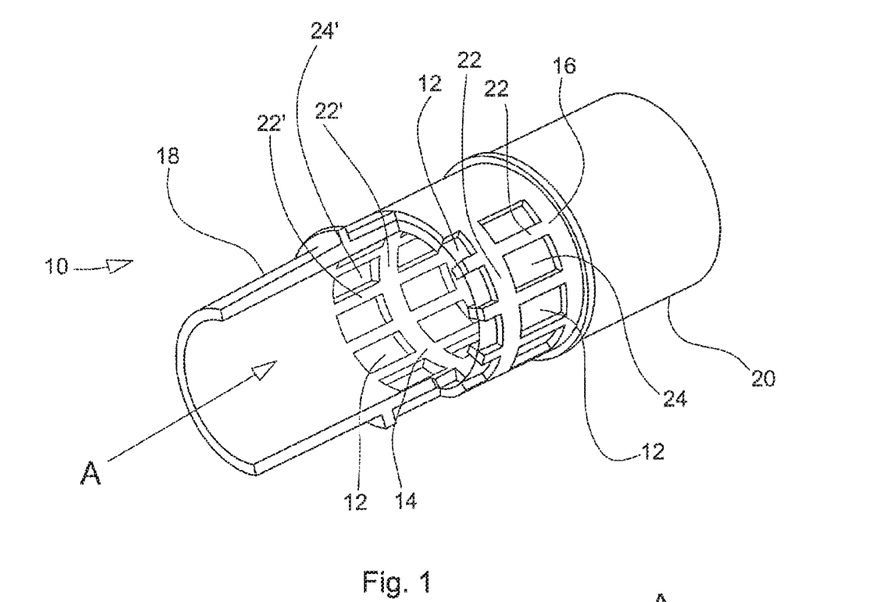
FIG. 1 shows a cut-away view of embodiment of the cartridge of the present invention.

Turning to the Figures, FIG. 1 shows a cut-away perspective view of an embodiment of the cartridge, 10, of the present invention. The cartridge, 10, contains a semipermeable membrane, 12, affixed between an inner cage, 14, and an outer cage, 16. The airflow direction is shown from left to right, according to arrow A. In this embodiment, the inner cage, 14, is connected to an upstream connector, 18, and a downstream connector, 20, opposite the upstream connector, 18.

In this embodiment, the semipermeable membrane, 12, is permanently-affixed and therefore not removable, from between the inner cage, 14 and the outer cage, 16, as the outer cage, 16 is sealed closed around the semipermeable membrane, 12, and the inner cage, 14. This may be accomplished by any of many processes known in the art, for example, ultrasonic sealing adhesives, heat-sealing, etc. The outer cage, 16, is therefore located in a position that is exterior to the inner cage, 14, and the semipermeable membrane, 12. Conversely, the inner cage, 14, is located interior to the outer cage, 16.

The outer cage, 16, for example, may be formed with thicker, distinct boundaries, 22, which form a plurality of open cells, 24. As the boundaries, 22, cover the semipermeable membrane, 12, water vapour may not flow through the semipermeable membrane, 12 at the specific locations where it is covered by the boundaries, 22. Instead, the water vapour is able to pass through the semipermeable membrane, 12, at locations such as where the open cells, 24, are located. Similarly, in FIG. 1, the inner cage, 14, contains boundaries, 22', which also form open cells, 24'. In an embodiment herein, the majority of the open cells of the outer cage match up at least partially; or completely, with the open cells of the inner cage.

In an embodiment herein, the outer cage is formed with a plurality of boundaries, while the inner cage contains fewer boundaries, or may essentially contain none or a single boundary; or a single open cell. In an embodiment herein, the inner cage is formed with a plurality of boundaries, while the outer cage contains fewer boundaries, or may essentially contain none or a single boundary; or a single open cell. In an embodiment herein, the inner cage and the outer cage are formed with complementary boundaries; or essentially the same pattern of boundaries; or the same number and pattern of open cells.

Without intending to be limited by theory, it is believed that the structure of a series of boundaries forming a plurality of open cells provides a good balance between providing structural integrity to reduce; or prevent unintended tearing of the semipermeable membrane, reducing manufacturing complexity and cost, and/or providing sufficient area so as to maximize the cartridge's WVTR.

Figure 2:
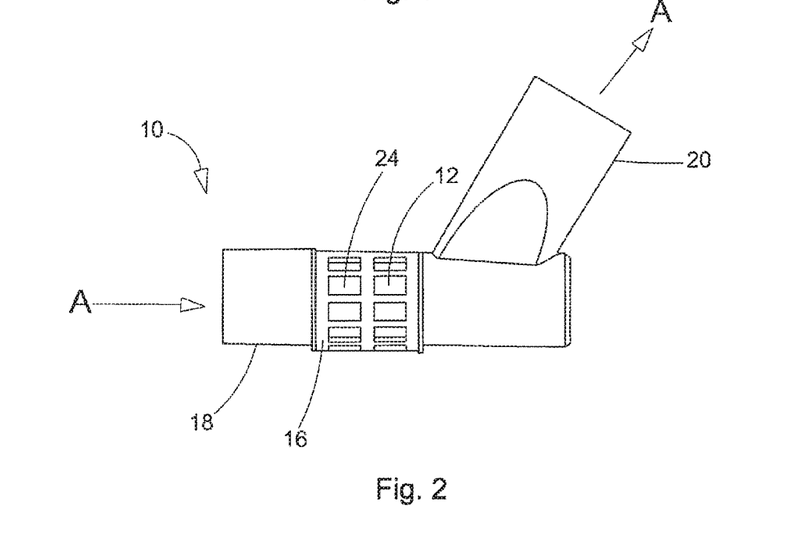
FIG. 2 shows an embodiment of a cartridge having an outer cage connected to an upstream connector and a downstream connector.

FIG. 2 shows an embodiment of a cartridge, 10, having an outer cage, 16, connected to an upstream connector, 18, and a downstream connector, 20. The airflow direction is indicated by Arrow, A. The cartridge, 10, further contains a semipermeable membrane, 12, which is visible in the open cells, 24, of the outer cage, 16. The upstream connector, 18, and/or the downstream connector, 20, further connect with the breathing circuit (see FIG. 4 at 26).

Figure 3:
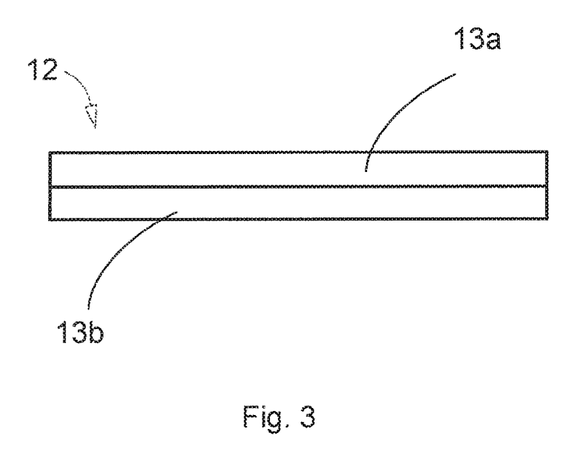
FIG. 3 shows a schematic diagram of the cross-section of an embodiment of the semipermeable membrane of the present invention.

FIG. 3 shows a schematic diagram of the structural arrangement of an embodiment of the semipermeable membrane, 12. The semipermeable membrane, 12, includes a poly(tetrafluoroethylene) membrane, 13a, and a coating containing graphene anti-bacterial compound, 13b. The semipermeable membrane, 12, is affixed between the inner cage (see FIG. 1 at 14) and the outer cage (see FIG. 1 at 16) with the poly(tetrafluoroethylene) membrane, 13a, facing externally, towards the external environment and the coating, 13b, facing inwardly. One advantage of this positional arrangement is that the coating, 13b, can effectively absorb the water vapour in the respiratory gas and pass it to the poly(tetrafluoroethylene) membrane, 13a, for evaporation. The permeability of the poly(tetrafluoroethylene) membrane, 13a, to gas facilitates rapid evaporation of the water vapour and thus enhances water vapour transmission rate.

Figure 4:
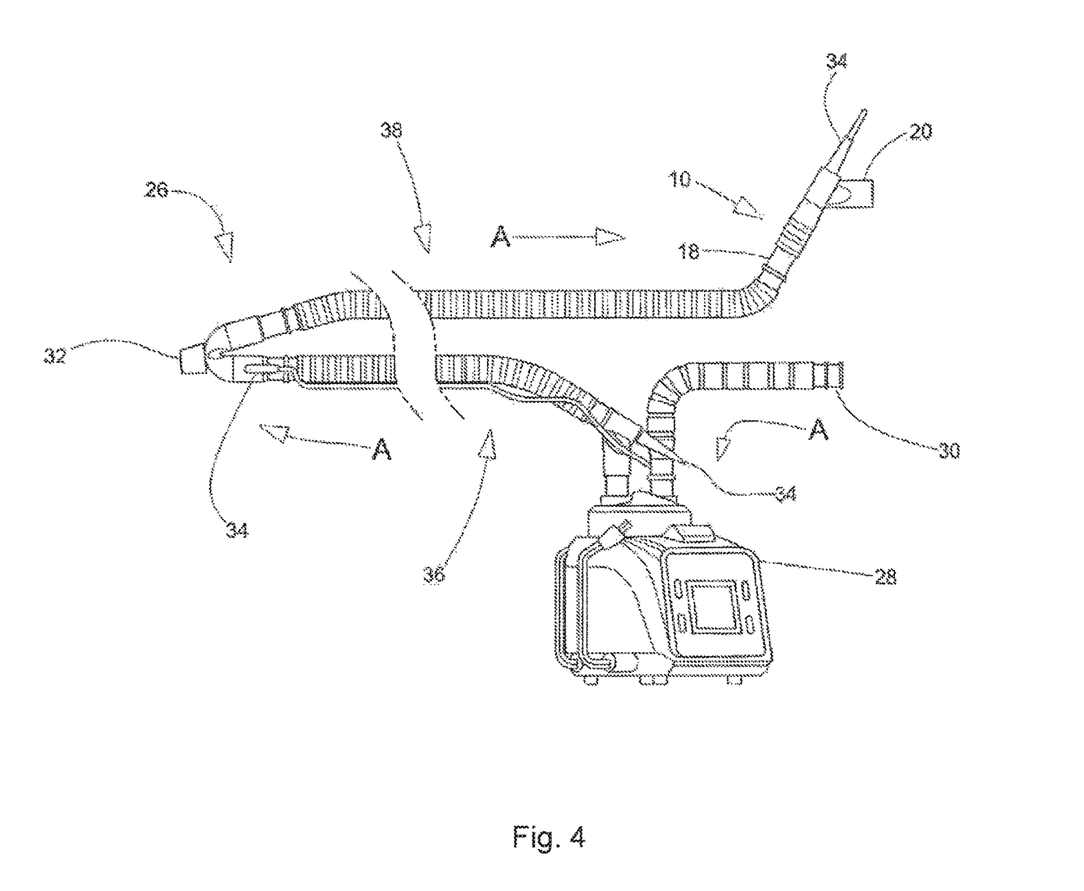
FIG. 4 shows an embodiment of a breathing circuit of the present invention containing a cartridge.

FIG. 4 shows an embodiment of a breathing circuit, 26, of the present invention, containing a cartridge, 10. The airflow direction is indicated by Arrow, A. The cartridge, 10, is attached to the breathing circuit, 26, at the upstream connector, 18. The breathing circuit, 26, is also connected to a humidifier, 28, and has an upstream end, 30. The upstream end, 30, would typically be connected to, for example, a ventilator.

In FIG. 4, the cartridge, 10, is located downstream of a mouthpiece, 32, which is the position from which the user; or patient, breathes. It is understood that in an embodiment of the present invention, the mouthpiece may be replaced with, for example, a nasal attachment, a trachea attachment, (anything else), and a combination thereof, as desired.

In the embodiment of FIG. 4, the breathing circuit, 26, contains a plurality of optional sensor attachments, 32, which are provided to potentially detect, for example, the temperature, humidity, airflow rate, $O_2$ concentration, $CO_2$ concentration, and a combination thereof; or the temperature, humidity, and a combination thereof; or the temperature, of the air in the breathing circuit. The sensor attachment may further be connected to, for example, a computer, alarm system, or instrument panel (not shown) as desired.

The breathing circuit, 26, typically contains an inhalatory limb, 36, and an exhalatory limb, 38. The inhalatory limb is defined as the portion of the breathing circuit, 26, stretching from the humidifier, 28, to the mouthpiece, 32. The exhalatory limb, 38, is defined as the portion of the breathing circuit, 26, stretching from the mouthpiece, 32, to the upstream connector, 18. The exhalatory limb, 38, and/or the inhalatory limb, 36, may also contain the various sensor attachments, 34, as well.

The breathing circuit herein may be, for example, as shown in FIG. 1, but is not limited thereto. The breathing circuit and/or the breathing system may be in another configuration as desired. For example, breathing circuits and/or breathing systems having coaxial lumens, multiple lumens, multiple limbs, Y-shaped limbs, etc. are known and may be useful herein.

The breathing circuit, 26, in FIG. 4 is an adult breathing circuit, as is typically found in hospitals, with the addition of the cartridge as described herein. However, all types and sizes of breathing circuits are also contemplated and believed to be within the scope of the present invention, such as, for example, an adult breathing circuit, a neonatal breathing circuits, a child breathing circuit, and a combination thereof; or an adult breathing circuit, a neonatal breathing circuit, and a combination thereof; or an adult breathing circuit.

As noted above, it is common for a breathing circuit; or an adult breathing circuit which contains a water vapour permeable material such as a foamed poly(tetrafluoroethylene) side wall/tube, to absorb moisture during use. However, as noted above, it is desirable to reduce the weight of such a breathing circuit. Without intending to be limited by theory, it is believed that the present invention provides similar moisture release from the air inside of the breathing circuit, while simultaneously absorbing less moisture from the air inside of the breathing circuit. Accordingly, in an embodiment of the present invention, the breathing circuit is an adult breathing circuit and the breathing circuit absorbs less than or equal to about 82 g of moisture; or from about 82 g to about 0 g of moisture; or from about 80 g to about 0 g of moisture; or from about 75 g to about 0 g of moisture; or from about 70 g to about 0 g of moisture, over 24 hours.

The breathing circuit herein is often attached to a breathing system having, for example, a breathing system machine (e.g., a ventilator, a pump, a humidifier, a heater, a continuous positive airway pressure (a.k.a., CPAP) machine, etc. and a combination thereof) and lead from the machine to the user and then may further lead back to the machine or elsewhere. Oftentimes, the breathing system machine may also heat and/or humidify the air so as to make it easier and/or more comfortable for the user to breathe.

In an embodiment herein, the breathing circuit includes a hose attached either directly or indirectly to the cartridge herein. In an embodiment herein, the hose is formed of a foamed plastic, and is typically a thicker foamed plastic so as to provide better insulation to reduce heat loss from the air inside of the tube.

In an embodiment herein, the cartridge is located in the breathing circuit near, or adjacent to the exhalatory limb; or next to or adjacent to where the patient exhales into the exhalatory limb, as this is the position of greatest water vapour concentration. Without intending to be limited by theory, it is believed that if the cartridge can help to reduce the concentration of water vapour/humidity at this point, the overall risk of condensation and water entrapment is reduced.

Example 1

Moisture Absorption Test

The test method used herein for measuring the moisture absorbed by a breathing circuit over 24 hours is as follows:
1. The breathing circuit, including the inhalatory limb, and the exhalatory limb, are weighed on an electronic scale prior to any use so as to establish a baseline.
2. A humidifier and heater are connected to the breathing circuit and set to provide a constant humidity of 45%-65% and a temperature at the mouthpiece of 37° C. (±2° C.). The air outside of the breathing circuit is kept at 20° C. (±2° C.). A ventilator is set at a frequency of 20 bpm and a tidal volume of 500 ml for an adult breathing circuit. For a neonatal breathing circuit, the frequency is set at 40 bpm, and the tidal volume is 80 ml.
3. A simulated lung is attached to the mouthpiece, and the humidifier, heater, and ventilator are run for 24 hours.
4. The breathing circuit is disconnected and weighed, and the baseline is subtracted to determine the amount of moisture absorbed by the breathing circuit.

In a comparative example, an existing breathing circuit is purchased from Fisher & Paykel of Auckland, New Zealand (Evaqua II adult circuit with an inhalatory limb formed of polyethylene and an exhalatory limb formed of extruded poly(tetrafluoroethylene)) and is subject to the Moisture Absorption Test, herein.

An inventive example employs a breathing circuit from Vincent Medical Care Co. of Hong Kong (adult Liqfree circuit formed of extruded polyethylene) is connected to a cartridge as described herein. The cartridge contains a semipermeable membrane containing a poly(tetrafluoroethylene) membrane 100 μm thick, sprayed with a graphene anti-bacterial coating 3-5 μm thick. The cartridge has an inner cage and an outer cage exterior to the inner cage. The semipermeable membrane is permanently-affixed between the inner cage and the outer cage. The cartridge has a surface area (i.e., of the inside of the cartridge) of 0.003 $m^2$ (about 8.6 cm wide and 3.6 cm high) and a WVTR of ≥1.01 g $H_2O$/hour. Approximately 5% of the semipermeable membrane surface is directly occluded by the inner cage and outer cage. The inventive example is subject to the Moisture Absorption Test, herein.

TABLE 1

| | Initial Breathing Circuit Weight | Breathing Circuit Weight after 24 hours | Absorbed moisture | % weight increase |
|---|---|---|---|---|
| Evaqua (Comparative) | 244.5 g | 330 g | 85.5 g | 35% |
| Liqfree + Cartridge (Inventive) | 231.2 | 293.7 | 62.5 g | 27% |

From the above, it can be seen that the inventive breathing circuit absorbed only 62.5 g of moisture which is significantly less moisture than the 85.5 g of water absorbed by the comparative breathing circuit. Furthermore, when viewed as a percentage increase in the weight of the breathing circuit, it can be seen that the inventive breathing circuit containing the cartridge of the invention herein had a much lower weight increase after simulating 24 hours of use.

Example 2

An embodiment of the semipermeable membrane of the present invention is subject to an antibacterial test in accordance with the Chinese Standard GB/T2591-2003, Antimicrobial plastics—Test for antimicrobial activity, and water vapour transmission rate test. The semipermeable membrane is prepared by spraying thereupon a mixture containing the graphene anti-bacterial compound on the poly(tetrafluoroethylene) membrane, and drying. The mixture is prepared according to the following formulation:

TABLE 2

| Component(s) | Amount (% by weight) |
|---|---|
| Graphene nano-platelets | 0.1-0.5% |
| Antioxidant | 0.5-2% |
| Benzylamine hydrochloride | 0.1-0.3% |
| Styrenic block copolymer thermoplastic elastomer | 90-98% |
| Additive | 1-5% |

In the antimicrobial test, it is found that the antimicrobial activity of the semipermeable membrane is at the level 0, which means it possesses strong antiseptic effect and good self-cleaning effect.

Figure 5:
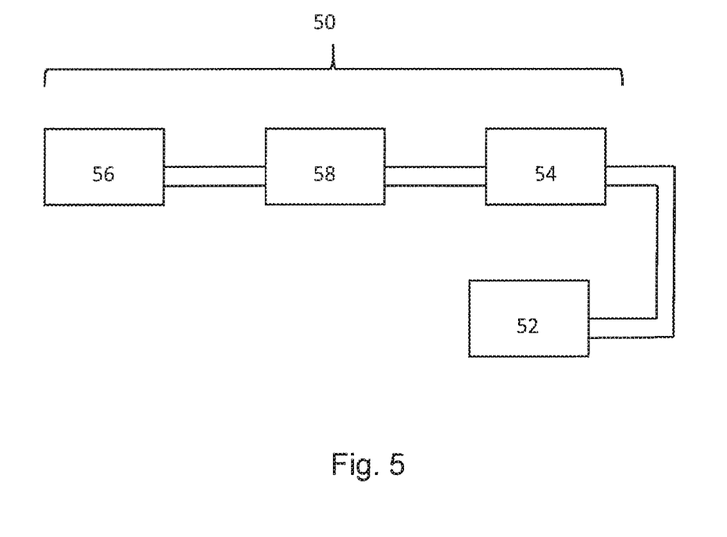
FIG. 5 shows a set-up of a water vapour transmission rate (WVTR) measuring device for determining the WVTR of the semipermeable membrane of the present invention. The figures herein are for illustrative purposes only and are not necessarily drawn to scale.

In the water vapour transmission rate test, 2 samples of the semipermeable membrane, membranes A and B, prepared according to the above are tested. The samples have a size of 75×75 mm. The test is performed with a water vapour transmission rate measuring device as illustrated in FIG. 5, and includes the following steps:

The water vapour transmission rate (WVTR) measuring device, 50, is connected to the pressurized nitrogen gas (a gas source), 52, the measuring device is equipped with a flow meter, 54, and a molecular sieve, 56. 13.5 g of purified water is added to the water tank (65×65 mm), 58, of the WVTR measuring device, and it is the best to have the water level 2 mm below the top surface of the water tank, 58.

One semipermeable membrane is placed into the WVTR measuring device, 50, particularly positioned in the water tank, 58, without contacting the water. The semipermeable membrane is affixed by upper and lower fastening plates with the coating side facing towards water.

The WVTR measuring device, 50, is connected to the power, and the temperature for test is set at 30° C. The heating process starts.

When the WVTR measuring device, 50, is stable at the temperature of 30° C., the nitrogen gas valve is opened to supply nitrogen to the device, 50, at a pressure of 0.5 MPa, and the flow is adjusted to 1.03±0.03 L/min.

Before the test, the molecular sieve, 56, positioned at the end portion of the WVTR measuring device, 50, is removed and weighed by electronic balance. The weight measured is recorded as $m_1$. Then, the test is started and the time period is recorded.

After 10 min, the molecular sieve, 56, is removed and weighed again, the weight measured is recorded as $m_2$.

The WVTR in unit of $g/(m^2 \times min)$ is calculated with the formula:

$$WVTR=(m_2-m_1)/(10\times0.065\times0.065).$$

The molecular sieve, 56, is then replaced with a new one. The test is repeated for 4 times for the same semipermeable membrane.

The above steps are repeated for the second semipermeable membrane.

According to one embodiment of the present invention, it is preferred that the minimal WVTR is at least 5.47 $g/(m^2 \cdot min)$, i.e. at least 328.2 $g/(m^2 \cdot hour)$.

The test results of semipermeable membrane A and B are as follows.

TABLE 3

| Sample Time(s) | Initial weight $(m_1)$ g | Final weight $(m_2)$ g | $m_2 - m_1$ g | Time min | WVTR $g/(m^2 \times min)$ |
|---|---|---|---|---|---|
| Semipermeable membrane A | | | | | |
| $1^{st}$ | 187.2 | 187.5 | 0.3 | 10 | 7.10 |
| $2^{nd}$ | 189.3 | 189.6 | 0.3 | 10 | 7.10 |
| $3^{rd}$ | 190.0 | 190.3 | 0.3 | 10 | 7.10 |
| $4^{th}$ | 188.6 | 188.9 | 0.3 | 10 | 7.10 |
| $5^{th}$ | 190.0 | 190.3 | 0.3 | 10 | 7.10 |
| Semipermeable membrane B | | | | | |
| $1^{st}$ | 188.0 | 188.3 | 0.3 | 10 | 7.10 |
| $2^{nd}$ | 190.0 | 190.3 | 0.3 | 10 | 7.10 |
| $3^{rd}$ | 189.2 | 189.5 | 0.3 | 10 | 7.10 |
| $4^{th}$ | 186.6 | 186.9 | 0.3 | 10 | 7.10 |
| $5^{th}$ | 185.1 | 185.5 | 0.4 | 10 | 9.47 |

The WVTR of both semipermeable membranes A and B exceeds 5.47 g/(m²×min), and therefore these membranes are suitable for used in cartridge of the present invention. These semipermeable membranes can effectively remove water vapour from the respiratory gas.

An embodiment of the present invention also relates to a breathing circuit containing the cartridge herein.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

What is claimed is:

1. A cartridge for a breathing circuit comprising:
   A. semipermeable membrane comprising:
      i. a poly(tetrafluoroethylene) membrane; and
      ii. a graphene anti-bacterial compound;
   B. an outer cage; and
   C. an optional inner cage interior to the outer cage,
   wherein the semipermeable membrane is affixed to the outer cage, and optionally between the inner cage and the outer cage, and wherein the graphene anti-bacterial compound is provided in a layer on the poly(tetrafluoroethylene) membrane, the layer further comprises a thermoplastic elastomer, an additional anti-bacterial compound, and optionally an antioxidant and an additive.

2. The cartridge according to claim 1, wherein the graphene anti-bacterial compound is sprayed onto the poly(tetrafluoroethylene) membrane.

3. The cartridge according to claim 1, wherein the poly(tetrafluoroethylene) membrane has a thickness of from about 1 μm to about 1 mm.

4. The cartridge according to claim 1, wherein the poly(tetrafluoroethylene) membrane has a water vapour transmission rate of from about 10 g $H_2O$/(hour×m²) to about 1000 g $H_2O$/(hour×m²).

5. The cartridge according to claim 1, further comprising an upstream connector connected to the outer cage and a downstream connector connected to the outer cage, wherein the upstream connector and/or the downstream connector is attachable to a breathing circuit.

6. The cartridge according to claim 1, wherein the semipermeable membrane is removably-affixed to the outer cage, or optionally between the inner cage and the outer cage.

7. The cartridge according to claim 1, wherein the semipermeable membrane has a surface area of from about 5 cm² to about 100 cm².

8. The cartridge according to claim 1, wherein the semipermeable membrane is affixed to the inner surface of the outer cage.

9. The cartridge according to claim 1, wherein the additional anti-bacterial compound is benzylamine hydrochloride or a quaternary ammonium compound.

10. The cartridge according to claim 1, wherein the layer comprises hydrophilic pores allowing water vapour to pass through.

11. The cartridge according to claim 10, wherein the hydrophilic pores have an average diameter of about 1 nm or less than 1 nm.

12. A breathing circuit comprising a cartridge according to claim 1.

13. The breathing circuit according to claim 12, wherein the cartridge is located downstream from a user.

14. The breathing circuit according to claim 12, wherein the breathing circuit is an adult breathing circuit and wherein the breathing circuit absorbs less than about 82 g of moisture in a 24-hour period.

15. The breathing circuit according to claim 12 wherein the breathing circuit is a neonatal breathing circuit and wherein the breathing circuit absorbs less than about 8 g of moisture in a 24-hour period.

16. The breathing circuit according to claim 12, further comprising a hose, wherein the hose comprises a foamed plastic.

17. A breathing system comprising:
   A. the breathing circuit according to claim 12; and
   B. a breathing system machine.

* * * * *